United States Patent [19]

Olson et al.

[11] Patent Number: 5,676,953
[45] Date of Patent: *Oct. 14, 1997

[54] INTESTINAL PROTOZOAL VACCINES

[75] Inventors: Merle E. Olson; Howard Ceri, both of Calgary; Douglas W. Morck, Airdrie, all of Canada

[73] Assignee: University Technologies International, Inc., Alberta, Canada

[*] Notice: The term of this patent shall not extend beyond the expiration date of Pat. No. 5,512,288.

[21] Appl. No.: 463,868

[22] Filed: Jun. 5, 1995

Related U.S. Application Data

[62] Division of Ser. No. 294,047, Aug. 24, 1994, Pat. No. 5,549,899, which is a continuation of Ser. No. 985,489, Dec. 4, 1992, abandoned.

[51] Int. Cl.$^6$ .............................. A61K 39/002; C12N 1/10
[52] U.S. Cl. ..................................... 424/269.1; 424/269.1; 424/265.1; 435/258.1
[58] Field of Search ....................... 424/269.1; 435/258.1

[56] References Cited

U.S. PATENT DOCUMENTS

| | | |
|---|---|---|
| 4,238,478 | 12/1980 | Stojkovic . |
| 4,314,992 | 2/1982 | Bitakaramire . |
| 4,404,186 | 9/1983 | Ron . |
| 4,493,825 | 1/1985 | Platt . |
| 4,639,372 | 1/1987 | Murray . |
| 4,687,666 | 8/1987 | O'Daly . |
| 4,724,145 | 2/1988 | Murray . |
| 4,808,404 | 2/1989 | Bhogal . |
| 4,837,016 | 6/1989 | Holder . |
| 5,028,694 | 7/1991 | Mewman . |
| 5,045,313 | 9/1991 | Frenkel . |
| 5,077,044 | 12/1991 | Stocker . |

OTHER PUBLICATIONS

Adam, The biology of Giardia spp., Microbiology Rev., 55 (4): 706–732 (1991).
Belosevic, et al., Observations on natural and experimental infections with giardia isolated from cats, Can. J. Comp. Med., 48:241–244 (1984).
Bemrick, et al., Giardiasis —is it really a zoonosis?, Parasitology Today, 4 (3): 69–71 (1988).
Bulow, et al., Protection of mice from fatal toxoplasma gandii infection by immunization with p30 antigen in liposomes[1], J. of Immun., 147 (10): 3496–3500 (1991).
Burst, et al., Pathophysiology of small intestinal mala absorption in gerbils infected with Giardia lamblia, Gastroenterology, 103:506–513 (1992).
Burst, et al., Growth, activities of enzymes in the small intestine, and ultrastructure of microvillus border in gerbils infected with Giardia duodenalis, Parasitol Res., 77:109–114 (1991).
Buret, et al., Effects of murine giardiasis on growth, intestinal morphology and disaccharidase activity, J. Parasitol, 76 (3): 403–409 (1990).
Buret, et al., Zoonotic potential of giardiasis in domestic ruminants, J. Infect. Dis., 162: 231–237 (1990).

Butscher, et al., The therapeutic action of monoclonal antibodies against surface glycoprotein of Giardia muris, Immunology, 64:175–180 (1988).
Buxton, et al., Vaccination of sheep with a live incomplete strain (S48) of toxoplasma gondii and their immunity to challenge when pregnant, Vet. Record, 129:89–93 (1991).
Capron, et al., Nouvelles approches moleculaires dans le diagnostic et la prevention de la toxoplasmose, Bull. Acad. Natle. Med., 174 (3): 387–394 (1990) (English version starts on p. 390).
Cesbron–Delauw, et al., Molecular characterization of a 23–kilodalton major antigen secreted by toxoplasma gondii, Proc. Natl. Acad. Sci. USA, 86:7537–7541 (1989).
Dahl, et al., Recognition by the human immune system of candidate vaccine epitopes of toxoplasma gondii measured by a competitive ELISA, Vaccine 5:187–191 (1987).
denHollander, et al., Immunology of Giardiasis, Parasitology Today, 4 (5): 124–130 (1988).
Duquesne, et al., Identification of T cell epitopes within a 23–kD antigen (P24) of toxoplasma gondii, Clin. Exp. Immun., 84:527–534 (1991).
Escajadillo, et al., Experimental toxoplasmosis and vaccine tests in aotus monkeys, Am. J. Trop. Med. Hyg. 44 (4): 382–389 (1991).
Farthing, et al., Mammalian bile promotes growth of Giardia lamblia in axenic culture, Transactions of The Royal Soc. of Trop. Med. and Hygiene, 77 (4): 467–469 (1983).
Faubert, Evidence that giardiasis is a zoonosis, Parasitology Today, 4 (3): 66–71 (1988).
Feingold, et al., Infect. Immun., 48(1 ): 211–218 (1985).
Feely, et al., The biology of Giardia, "Human Parasitic Diseases, 3: —Giardiasis", Meyer Ed., Elsevier Sci. Pub., 11–49 (1990).
Frenkel, et al., Prospective vaccine prepared from a new mutant of toxoplasma gondii for use in cat, Am. J. Vet. Res., 52 (10): 759–763 (1991 ).
Gazzinelli, Synergistic role of CD4[+] and CD8[+] T lymphocytes in ifnγ production and protective immunity induced by an attenuated toxoplasma gondii vaccine, J. of Immun., 146 (1): 286–292 (1991).
Gillin, et al., Secretory defenses against Giardia lamblia, Immun. of Milk and the Neonate, Mestecky, et al., Ed., Plenum Press, 227–233 (1991).
Gillin, et al., "Encystation and Expression of Cyst Antigens by Giardia lamblia in Vitro," Science:Materials Science, 235:1040–1043 (1987)

(List continued on next page.)

Primary Examiner—Paula K. Hutzell
Assistant Examiner—Khalid Masood
Attorney, Agent, or Firm—Burns, Doane, Swecker & Mathis, L.L.P.

[57] ABSTRACT

The invention provides vaccines and methods for preventing or treating intestinal protozoal infections in an animal. In particular, vaccines and methods for prevention or treatment of giardiasis are provided. The invention also encompasses methods of preparing and methods of use of novel toxins, antibodies, vaccine strains and compositions that result from or are used in these methods.

13 Claims, 6 Drawing Sheets

OTHER PUBLICATIONS

Gillin, et al., "Small-intestinal Factors Promote Encystation of *Giardia lamblia* in Vitro," Infection and Immunity, 56:705–707 (1988).

Gillin, et al., Exp, Parasitol., 69:164–174 (1989).

Gillon, et al., Changes in the small intestinal mucosa in giardiasis, "Giardia and Giardiasis", Erlandsen, et al., Eds., Plenum Press, 163–183 (1984).

Gottstein, et al., Human cellular immune response to *Giardia lamblia*, Infec., 19 (6): 421–426 (1991).

Grimwood, et al., Infect. Immun., 42(3): 1126–1135 (1983).

Halliday, et al., Transact. Royal Soc. Trop. Med. and Hyg., 82:428–432 (1988).

Hermentin, et al., Efforts towards a vaccine against toxoplasma gondii: a review, Zbl. Bakt. Hyg. A, 269:423–436 (1988).

Hewlett, et al., Experimental infection of mongrel dogs with *Giardia lamblia* cysts and cultured trophozoites, J. of Infec. Dis., 145 (1 ): 89–93 (1982).

Heyworth, Immunology of giardia and cryptosporidium infections, J. of Infec. Dis., 166: 465–472 (1992).

Heyworth, Relative susceptibility of giardia muris trophozoites to killing by mouse antibodies of different isotypes, J. Parasitol., 78 (1), 73–92 (1992).

Hill, et al., *Giardia lamblia* infection of suckling mice, J. of Infec. Dis., 147(2): 217–221 (1983).

Holmgren, FEMS Microbiol. Immunol. 89:1–10 (1991).

Istre, et al., Waterborne giardiasis at a mountain resort: evidence for acquired immunity, Am. J. Pub. Health, 74 (6): 602–604 (1984).

Jakubowski, Purple burps and the filtration of drinking water supplies, Am. J. Pub. Health, 78 (2): 123–125 (1988).

Janoff, et al., The role of immunity in Giardia infections, "Human Parasitic Diseases, 3: —Giardiasis", Meyer Ed., Elsevier Sci. Pub., 215–235 (1990).

Janoff, et al., Acute antibody responses to *Giardia lamblia* are depressed in patients with AIDS, J. Infec. Dis., 157 (4): 798–804 (1988).

Katelaris, et al., Diarrhoea and malabsorption in giardiasis: a multifactorial process? Gut., 33:295–297 (1992).

Katelaris, et al., Pathogenesis of diarrhea caused by *Giardia lamblia:* evidence for an exotoxin. J. Gastroenterol. Hepatol., 3 (suppl 1): A4 (1988).

Katelaris, et al., "Bile Modulates Genotypic and Phenotypic Characteristics of *Giardia Lamblia,*" Gut, 32:1089 (1991).

Keister, Axenic culture of *Giardia lamblia* in TYI–S–33 medium supplemented with bile, Transactions of The Royal Soc. of Trop. Med. and Hygiene, 77 (4): 487–488 (1983).

Kirkpatrick, et al., Feline giardiasis, observations on natural and induced infections, Am. J. Vet. Res., 45 (10): 2182–2188 (1984).

Ko, et al., Identification and characterization of a target antigen of a monoclonal antibody directed against *Eimeria tenella* morozoites, Molecular and Biochem. Parasitology, 41: 53–64 (1990).

Kum, et al., Indian J. Med. Res. 93: 40–46 (1991 ). Lewis, et al., Cortisone.

Lewis, et al., Cortisone–induced recrudescence of *Giardia lamblia* infections in gerbils, Am. J. Trop. Med. Hyg., 36 (1): 33–40 (1987).

Ljungstrom, et al., Immune response to *Giardia lamblia* in a water–borne outbreak of giardiasis in Sweden, J. Med. Microbiol., 36:347–352 (1992).

LoGalbo, et al., Symptomatic giardiasis in three patients with X–linked agammaglobulinemia, J. Pediatrics, 101 (1): 78–80 (1982).

McLeod, et al., Subcutaneous and intestinal vaccination with tachyzoites of *toxoplasma gondii* and acquisition of immunity to peroral and congenital toxoplasma challenge, J. of Immun., 140 (5): 1632–1637 (1988).

Marinculic, et al., Immunity in swine inoculated with larvae or extracts of a pig isolate and a sylvatic isolate of *Trichinella spiralis*, Am. J. Vet. Res., 52 (5): 754–763 (1991).

Mayrhofer, et al., The secretory immune response in rats infected with rodent *Giardia duodenalis* isolates and evidence for passive protection with immune bile, Adv. in Giardia Res., Wallis, et al., Eds., Univ. Calgary Press, Calgary, Alberta, Canada, 49–54 (1988).

Meloni; et al., Comparative studies on the axenic in vitro cultivation of giardia of human and canine origin: evidence for intraspecific variation, Transactions of The Royal Soc. of Trop. Med. and Hygiene, 81:637–640 (1987).

Meyer, Comparative studies on the axenic in vitro cultivation of giardia of human and canine origin: evidence for intraspecific variation, the epidemiology of giardiasis, Parasitology Today, 1 (4): 101–105 (1985).

Miller, et al., Characterization and vaccine potential of a novel recombinant coccidial antigen, Infec. and Immun., 57 (7): 2014–2020 (1989).

Morrow, et al., Protection against infection with *Giardia lamblia* by breast–feeding in a cohort of Mexican infants, J. of Pediatrics, 121 (3): 363–370 (1992).

Murtagh, et al., Guanine nucleotide–binding proteins in the intestinal parasite *g. lamblia*. Isolation of a gene encoding an approximately 20kDa 4DP–ribosylation factor, J. Biol. Chem., 267 (14): 9654–9655 (1992).

Nash, et al., Excretory–secretory products of *Giardia lamblia*, J. of Immun., 131 (4): 2004–2010 (1983).

Nash, et al., Exp. Parasitol., 68:238–241 (1989).

Overnes, et al., Immune response after immunization with an experimental *Toxoplasma gondii* ISCOM vaccine, Vaccine, 9, 25–28 (1991).

Ravdin, Entamoeba histolytica: pathogenic mechanisms, human immune response, and vaccine development, Clinical Res., 38 (2): 21 5–225 (1990).

Ravdin, Entamoeba histolytica: from adherence to enteropathy, J. of Infec. Dis., 159 (3): 420–429 (1989).

Reiner, et al., Human secretory and serum antibodies recognize environmentally induced antigens of *Giardia lamblia*, Infec. and Immun., 60 (2): 637–643 (1992).

Remington's Pharmaceutical Sciences, Mack Publishing Company, 1390 (1990).

Roach, et al., Transmission of *Giardia duodenalis* from human and animal sources in wild mice, "Advances in Giardia Research", Wallis, et al., Eds., Univ. Calgary Press, Calgary, Alberta, Canada, 79–82 (1988).

Roberts–Thomson, et al., Protection of mice against *Giardia muris* infection, Infect. and Immun., 24 (3): 971–973 (1979).

Roberts–Thomson, et al., Acquired resistance to infection in an animal model of giardiasis, J. of Immun., 117 (5): 2036–2037 (1976).

Saavera, et al., Human T cell clone identifies a potentially protective 54–kDa protein antigen of *Toxoplasma gondii* cloned and expressed in *Escherichia Coli*, J. of Immun., 147 (6): 1975–1982 (1991).

Schain, et al., Human T–lymphocyte proliferation, lymphokine production, and amebicidal activity elicited by the galactose–inhibitable adherence protein of *Entamoeba histolytica*, Infec. and Immun., 60 15): 2143–2146 (1992).

Shirley, Development of a live attenuated vaccine against coccidiosis of poultry, Parasite Immun., 11: 117–124 (1989).

Shirley, et al., Live attenuated coccidiosis vaccine: Selection of a second precocious line of eimeria maxima, Res. in Vet. Sci., 44:25–28 (1988).

Smith, et al. Chronic giardiasis: studies on drug sensitivity, toxin production, and host immune response. Gastroenterology, 83:797–803 (1982).

Steketee, et al., Recurrent outbreaks of giardiasis in a child day care center, Wisconsin, Am. J. Pub. Health, 79 (4): 485–490 (1989).

Stevens, et al., Local immunity in murine giardiasis: is milk protective at the expense of the maternal gut? Trans. Assoc. Am. Phys., 91:268–272 (1978).

Swabby, et al., Infection of mongolian gerbils (*Meriones unguiculatus*) with Giardia from human and animal sources, "Advances in Giardia Research", Wallis, et al., Eds., Univ. Calgary Press, Calgary, Alberta, Canada, 75–77 (1988).

Taylor, et al., Human immune response to *Giardia lamblia* infection, J. Infect. Dis., 155 (1): 137–140 (1987).

Tietz, et al., Interactions between sarcocystis gigantea lectin and toxin–containing fractions in human lymphocyte cultures, Parasitol. Res., 76: 32–35 (1989).

Vinayak, et al., Systemic —oral immunization with 56 kDa molecule of *Giardia lamblia* affords protection in experimental mice, Vaccine, 10 (1): 21–27 (1992).

Vinayak, et al., Alterations of humoral, cell mediated and antibody dependent cell mediated cytotoxic responses during the course of amoebic infection in guinea pigs, Gut, 28:1251–1256 (1987).

Wolfe, Giardiasis, Clin. Microbiology Rev., 5 (1): 93–100 (1992).

Wolfe, Clinical symptoms and diagnosis by traditional methods, Giardiasis, Meyer Ed., Elsevier Sci. Pub., 175–185 (1990).

Zaman, Dextran particles as a carrier for *Giardia lamblia* for scanning electron microscopy, J. Electron. Microsc., 41: 179–180 (1992).

Gupta et al Biol. Mem. 18(1,2):23–27, 1992.

Edson et al. (1986) Infec. Immunity 54 (3):621–625.

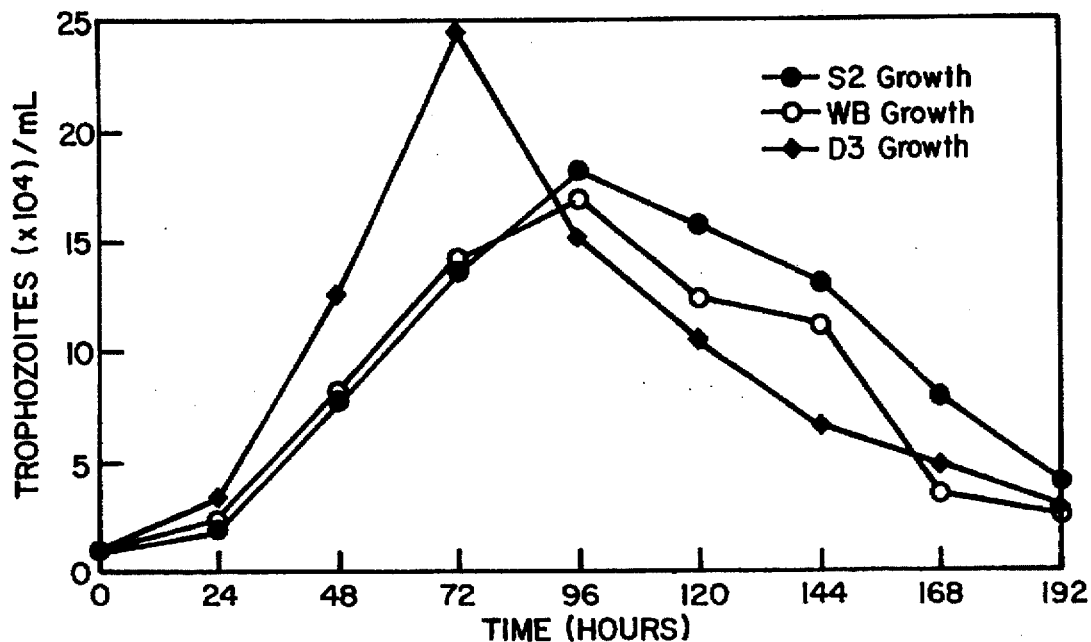
FIG_1
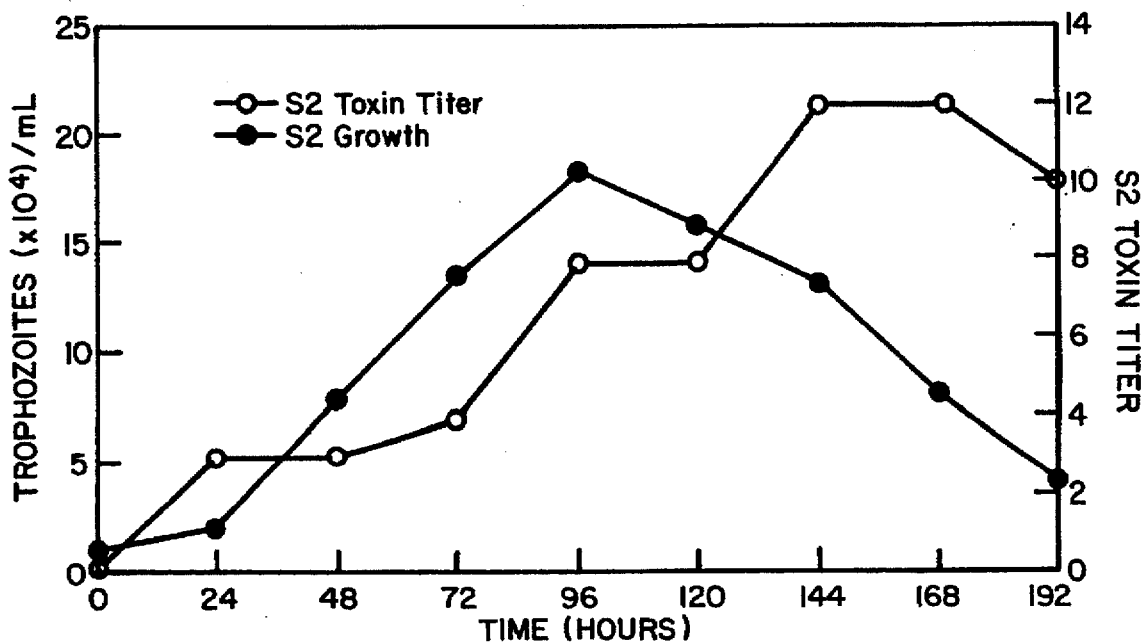
FIG_2

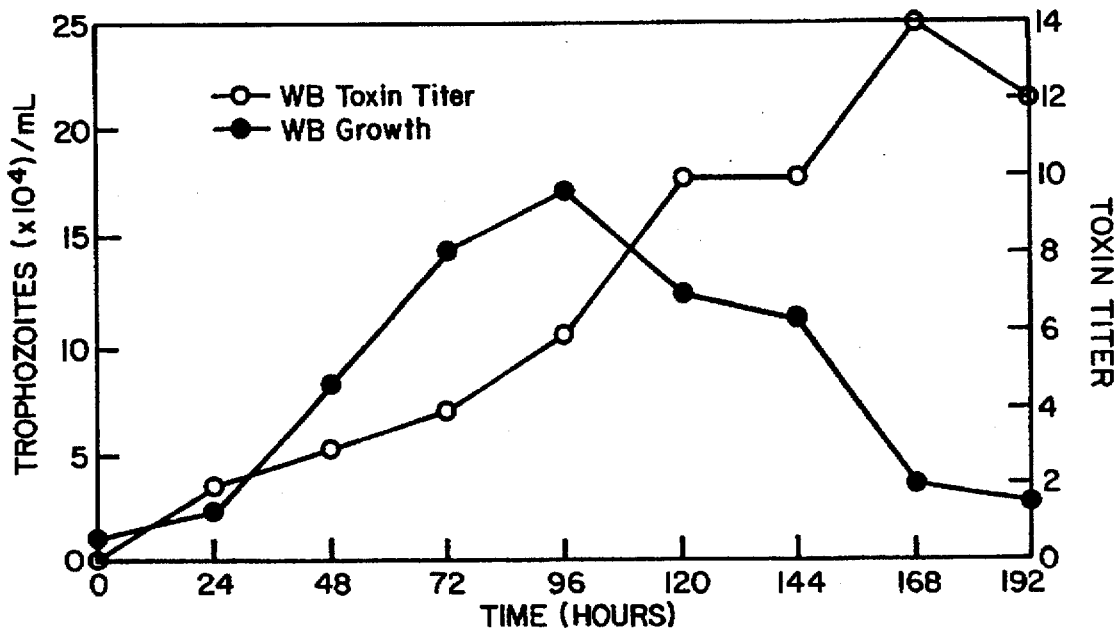
FIG_3
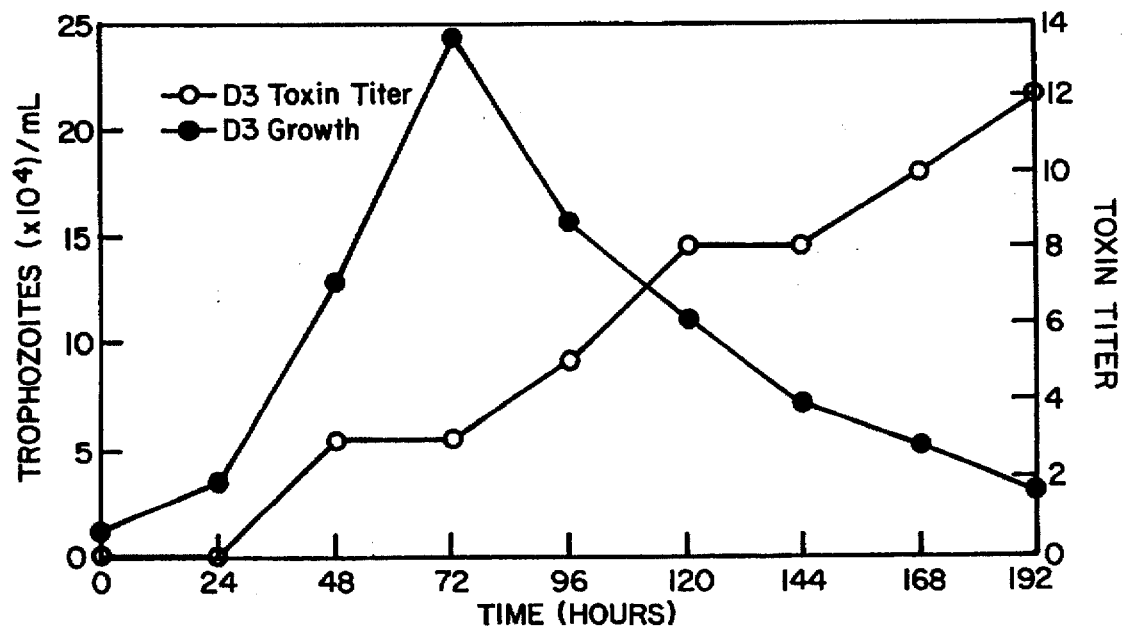
FIG_4

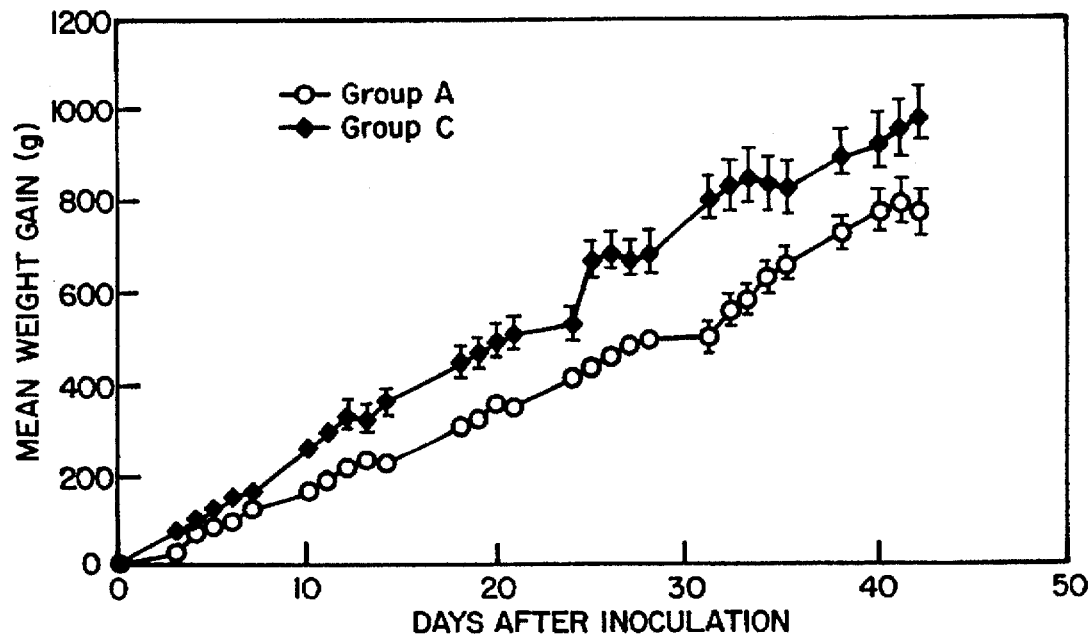
FIG_5
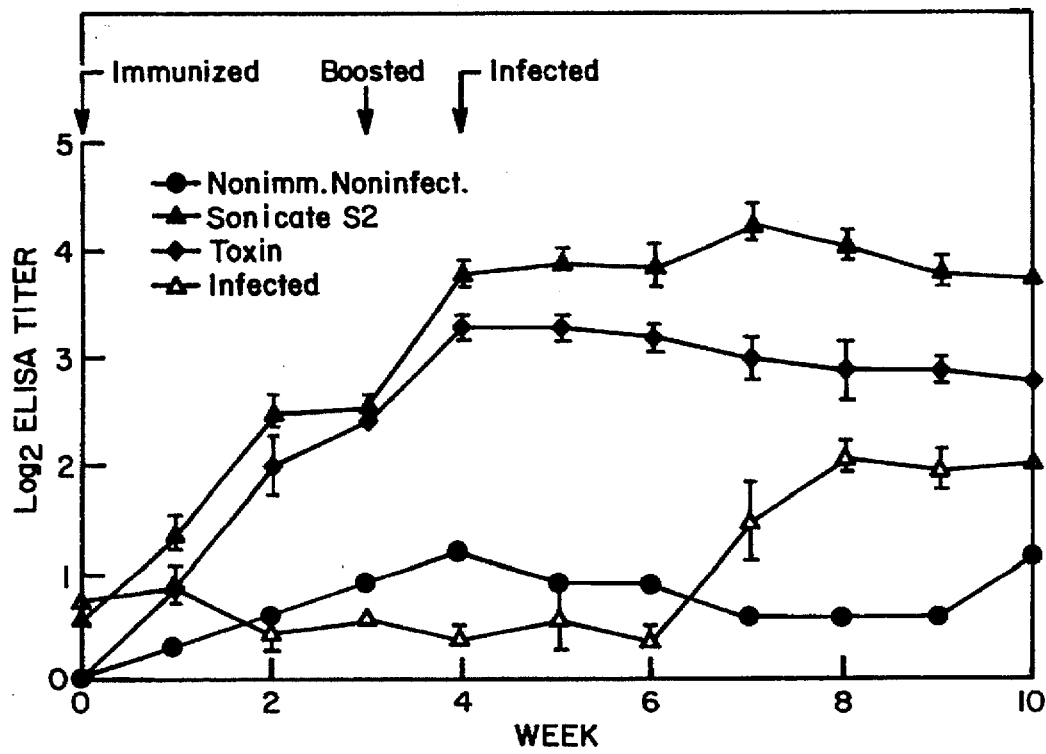
FIG_6

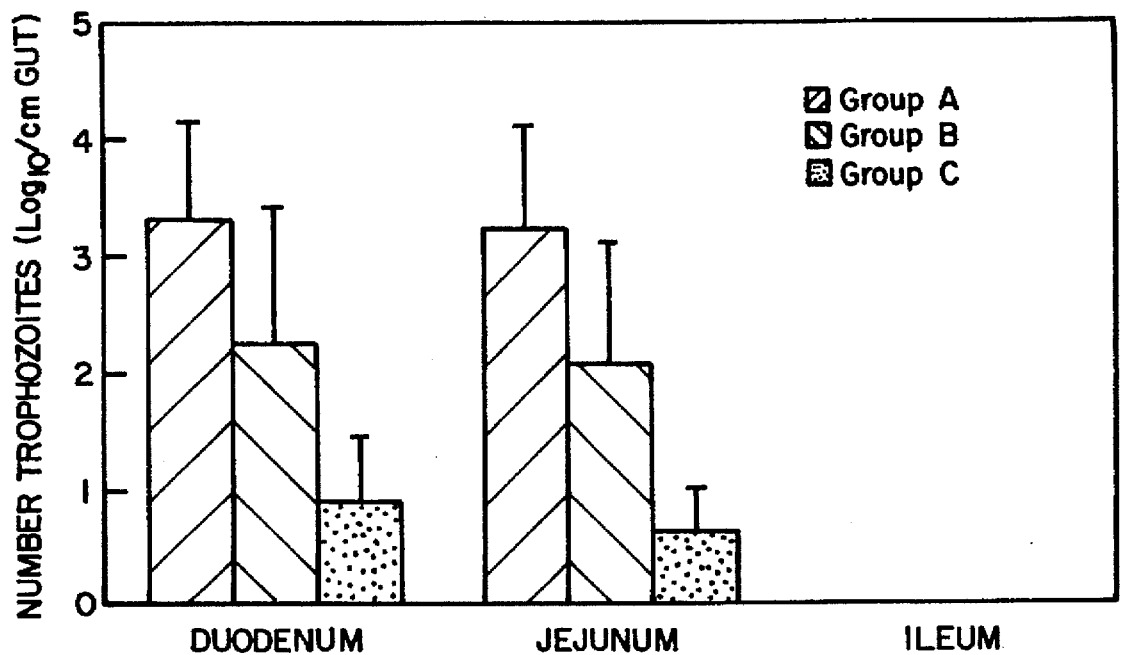
FIG_7
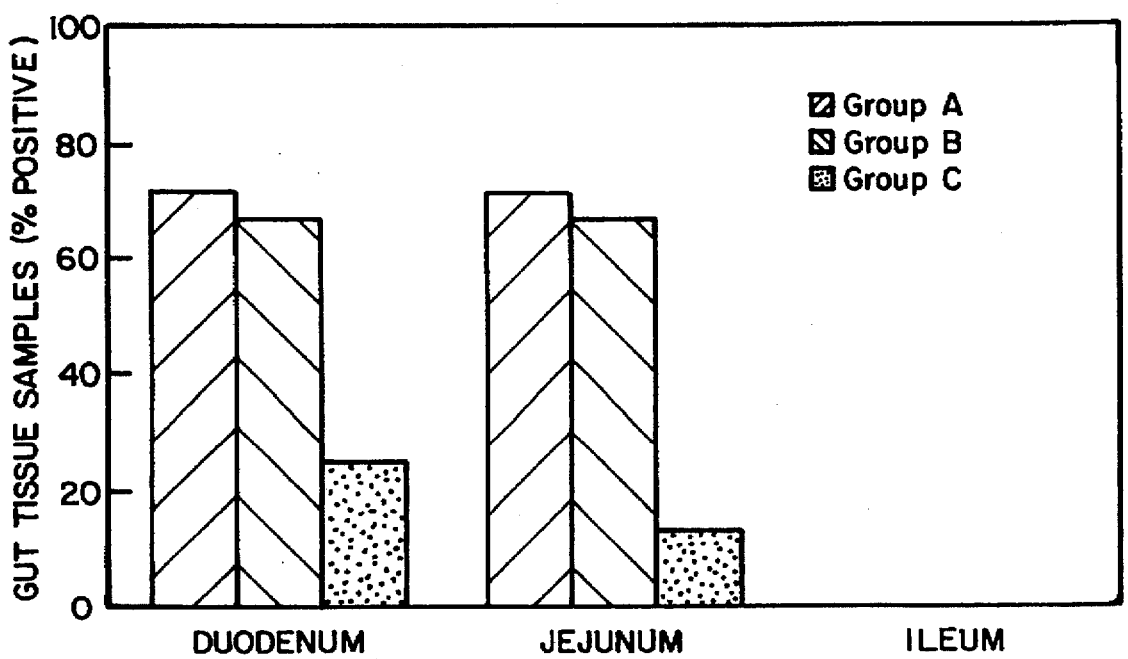
FIG_8

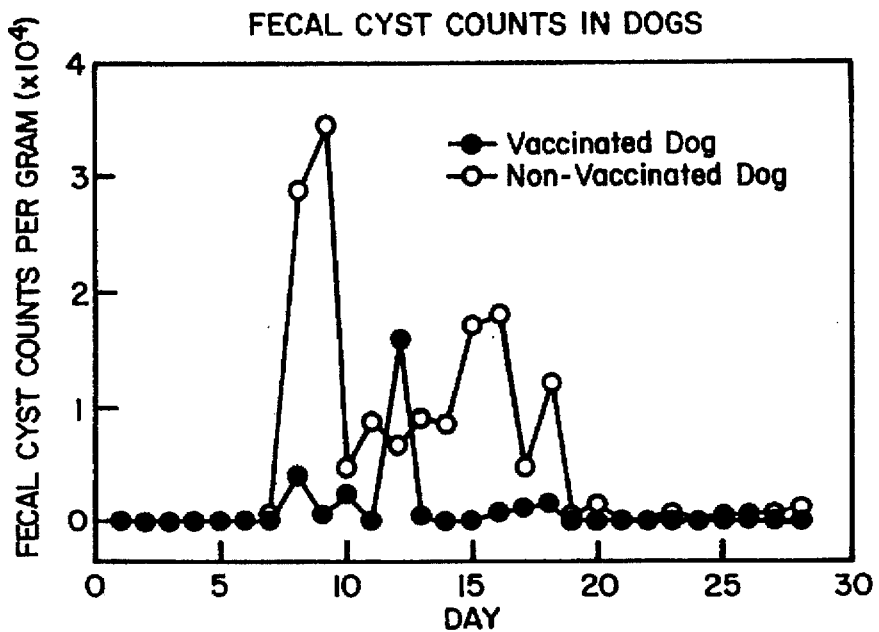
FIG_9
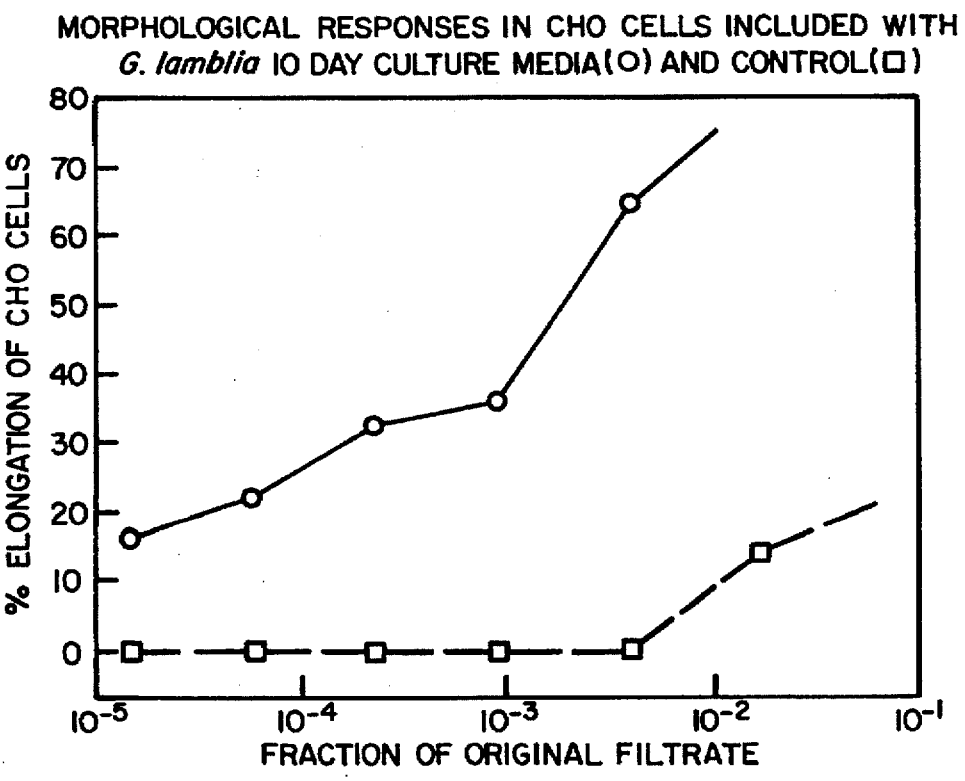
FIG_10

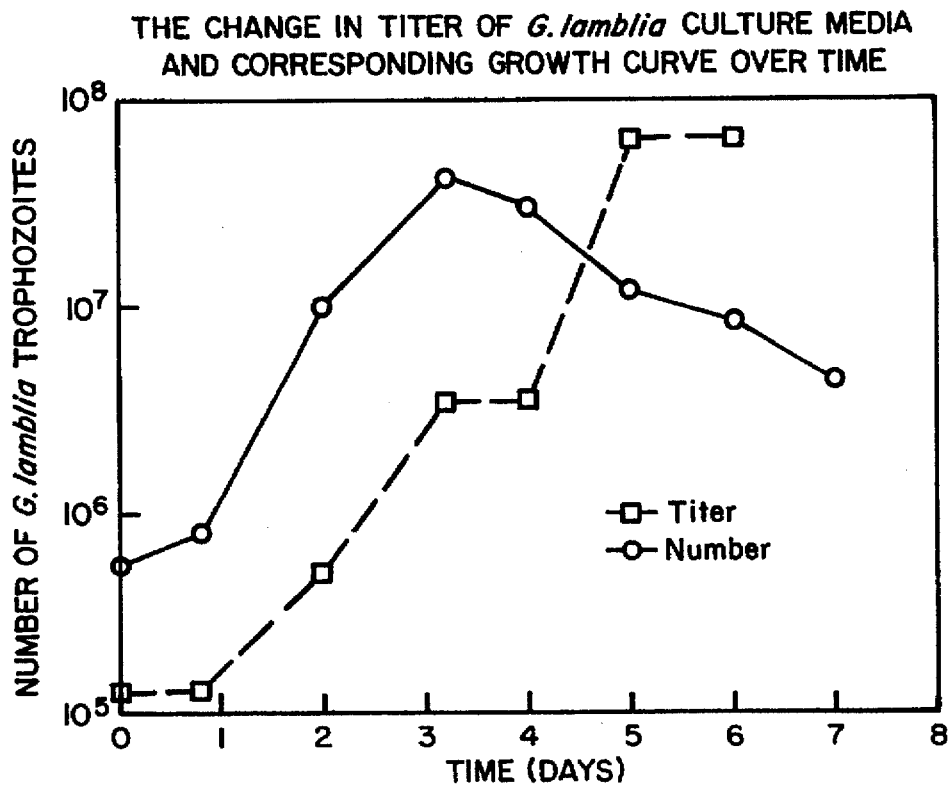
FIG_11
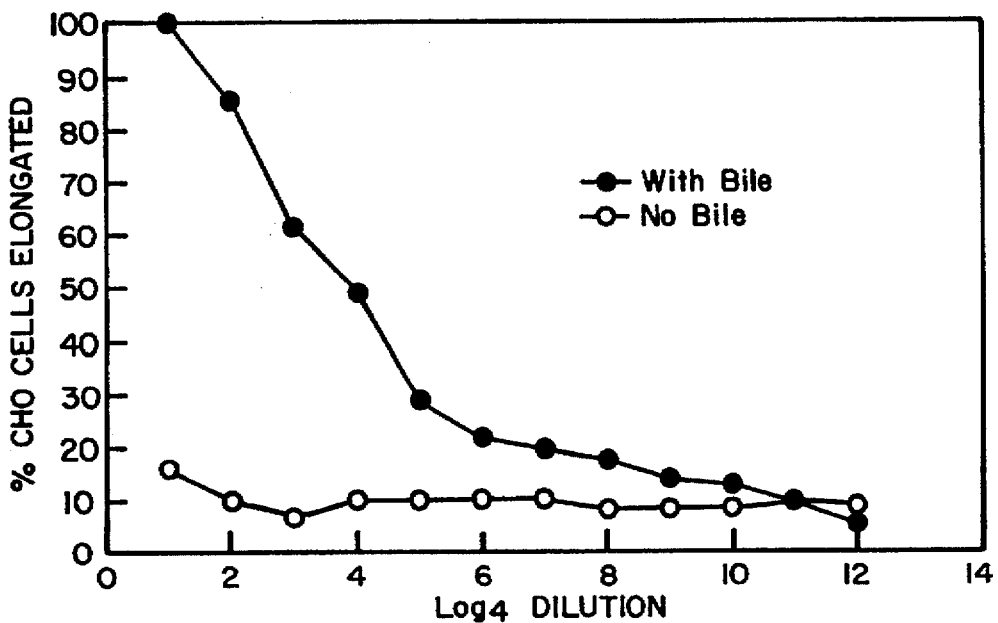
FIG_12

INTESTINAL PROTOZOAL VACCINES

This application is a divisional, of application Ser. No. 08/294,047, filed Aug. 24, 1994, (U.S. Pat. No. 5,549,899) which is a continuation of application Ser. No. 07/985,489, filed Dec. 4, 1992 (now abandoned).

FIELD OF THE INVENTION

The present invention relates to vaccines against intestinal protozoa. In particular, vaccines against Giardia are disclosed.

REFERENCES

The following references are cited in this application as superscript numbers at the relevant portions of the application.

1. Taylor, et al., Human immune response to *Giardia lamblia* infection, J. Infect. Dis., 155: 137–140 (1987).
2. Gillon, Changes in the small intestinal mucosa in giardiasis, "Giardia and Giardiasis", Erlandsen, et al., Eds., Plenum Press, New York, 163–183 (1984).
3. Wolfe, Clinical symptoms and diagnosis by traditional methods, "Human Parasitic Diseases, Volume 3—Giardiasis", Meyer Ed., Elsevier Science Publishers, New York, 175–186 (1990).
4. Feely, et al., The biology of Giardia, "Human Parasitic Diseases, Volume 3—Giardiasis", Meyer Ed., Elsevier Science Publishers, New York, 11–49 (1990).
5. Steketee, et al., Recurrent outbreaks of giardiasis in a child day care center, Wis. Am. J. Pub. Health 79: 485–490 (1989).
6. Faubert, Evidence that giardiasis is a zoonosis, Parasitology Today, 4 (3): 66–71 (1988).
7. Roach, et al., Transmission of *Giardia duodenalis* from human and animal sources in wild mice, "Advances in Giardia Research", Wallis, et al., Eds., Univ. Calgary Press, Calgary, 79–82 (1988).
8. Swabby, et al., Infection of mongolian gerbils (*Meriones unguiculatus*) with Giardia from human and animal sources, "Advances in Giardia Research", Wallis, et al., Eds., Univ. Calgary Press, Calgary, 75–77 (1988).
9. Jakubowski, Purple burps and the filtration of drinking water supplies, Am. J. Pub. Health, 78: 123–125 (1988).
10. Buret, et al., Zoonotic potential of giardiasis in domestic ruminants, J. Infect. Dis., 155: 137–140 (1987).
11. Vinayak, et al., Systemic oral immunization with 56 kDa molecule of *Giardia lamblia* affords protection in experimental mice, Vaccine 10: 21–27 (1992).
12. Buret, et al., Effects of murine giardiasis on growth, intestinal morphology and disaccharidase activity, J. Parasitol. 76 (3): 403–409 (1990).
13. Buret, et al., Growth, activities of enzymes in the small intestine, and ultrasonic of microvillus border in gerbils infected with *Giardia duodenalis*, Parasitol. Res. 77: 109–114 (1991).
14. Janoff, et al., The role of immunity in Giardia infections, "Human Parasitic Diseases, Volume 3—Giardiasis", Meyer Ed., Elsevier Science Publishers, New York, 215–235 (1990).
15. Lewis, et al., Cortisone-induced recrudescence of *Giardia lamblia* infections in gerbils, Am. J. Trop. Med. Hyg. 36 (1): 33–40 (1987).
16. Istre, et al., Waterborne giardiasis at a mountain resort: evidence for acquired immunity, Am. J. Public Health, 74 (6): 602–604 (1984).
17. den Hollander, et al. Immunology of Giardiasis. Parasitology Today. 4: 124–130 (1988).
18. Adam. The biology of Giardia spp. Microbiology Reviews. 55: 706–732 (1991).
19. Roberts-Thomson, et al. Acquired resistance to infection in an animal model of giardiasis. J. Immunology. 117: 2036–2037 (1976).
20. LoGalbo, et al. Symptomatic giardiasis in three patients with X-linked agammaglobulinemia. J. Pediat. 101: 78–80 (1982).
21. Janoff, et al. Acute antibody responses to *Giardia lamblia* are depressed in patients with AIDS. J. Infect. Dis. 157: 798–804 (1988).
22. Butscher, et al. The therapeutic action of monoclonal antibodies against surface glycoprotein of *Giardia muris*. Immunology. 64: 175–180 (1988).
23. Stevens, et al. Local immunity in murine giardiasis: is milk protective at the expense of the maternal gut? Trans. Assoc. Am. Phys. 91: 268–272 (1978).
24. Roberts-Thomson, et al. Protection of mice against *Giardia muris* infection. Infect. Immun. 24:971–973 (1979).
25. Smith, et al. Chronic giardiasis: studies on the drug sensitivity, toxin production, and host immune response. Gastroenterology. 83: 797–803 (1982).
26. Katelaris, et al. Diarrhea and malabsorption in giardiasis: a multifactorial process? Gut. 33: 295–297 (1992).
27. Nash, et al. Excretory-secretory products of *Giardia lamblia*. J. Immunology. 131: 2004–2010 (1983).
28. Katelaris, et al. Pathogenesis of diarrhea caused by *Giardia lamblia*: evidence for an exotoxin. J. Gastroenterol. Hepatol. 3(suppl 1): A4 (1988).
29. Zaman, Dextran particles as a carrier for *Giardia lamblia* for scanning electron microscopy, J. Electron. Microsc. 41: 179–180 (1992).
30. Kirkpatrick, et al., Feline giardiasis, observations on natural and induced infections, Am. J. Vet. Res., 45:2182–2188 (1984).

The disclosure of the above publications and patents are herein incorporated by reference in their entirety to the same extent as if the language of each individual publication or patent were specifically and individually included herein.

BACKGROUND OF THE INVENTION

Intestinal protozoa are the cause of many human and animal diseases. When they infect domestic animals, severe economic losses may result. Intestinal protozoa of importance include cryptosporidium, trichomonads, histomonas, spironucleus, entamoeba, coccidia, toxoplasma and sarcocystis. One of the most problematic intestinal protozoa is Giardia.

*Giardia lamblia* is the most commonly found pathogenic parasite in western countries and is endemic in much of North America[1]. Giardia is a flagellated protozoan which is transmitted through the fecal-oral route[2]. The mechanism of pathogenesis in Giardia is poorly understood but it results in symptoms similar to many other gastrointestinal ailments. The most common symptoms are diarrhea, anorexia, malaise, abdominal distention and flatulence. Acute stages of the infection usually last only a few days although occasionally, especially in children, the chronic stage may last for months[3].

Once inside its host, the *Giardia trophozoites* attach to the epithelium of host intestinal villi where they multiply, become encysted, and then are shed in the host feces. Some infected hosts become asymptomatic cyst passers after the short acute stage of the infection has passed[4].

A major source of Giardia infection is contaminated drinking water. This has earned it the name "backpackers diarrhea" because of the large number of people infected due to exposure to contaminated water when camping[4]. Outbreaks of giardiasis are also a frequent problem in day care centers. Recurring Giardia infections in day care centers are common, and many of the children are found to be carriers of the infection although they show no symptoms. This makes detection and effective treatment of Giardia in day care centers difficult[5].

A major area of interest in Giardia infections is the ability of animal hosts to act as reservoirs for human infective strains of Giardia. There is evidence that inter-species transmission of Giardia can and does occur. Human strains of Giardia have been shown to be infective in gerbils, mice, guinea pigs, raccoons, and beavers[6-8]. The common name given to Giardia infection in Canada, "beaver fever", was born when an epidemic of the infection resulted from the contamination of a water source by a family of three beavers[9]. Giardia infections are common in dogs and cats. It is estimated that 10–68% of dogs and 25% of cats are infected with Giardia. Studies of the prevalence of Giardia infection in domestic ruminants found infection in 17.7% of sheep and 10.4% of cattle, with the incidence being higher in lambs (35.6%) and calves (27.7%)[10].

As previously stated, clinical giardiasis may range from asymptomatic carriage of the parasite to an illness characterized by diarrhea, abdominal cramps, headache, gas, bloat, dehydration and malaise[1,11]. Weight loss and retardation of growth are also common problems associated with giardiasis in humans and animals[11].

In humans, histological changes associated with Giardia include villus atrophy[2]. More recent studies using Mongolian gerbils as an animal model have shown diffuse shortening of the microvillus mainly in the duodenum as well as a decrease in the brush border enzyme activity. The enzyme deficiencies may be caused by the shortening of the epithelial microvilli[12]. Other studies have correlated Giardia infection with decreased weight gain, decreased food intake, decreased intestinal disaccharidase activities and villus atrophy[13]. The diffuse shortening of microvillus may be the result of a toxin produced by the Giardia[12].

Given the prevalence of giardiasis and the difficulty in treating all those who are infected due to asymptomatic carriers, the development of a vaccine against Giardia is highly desirable. It has been shown that hosts will raise an immune response to Giardia and that they can retain long lasting immunity after the primary infection[14,15]. If a host is repeatedly exposed to Giardia, the risk of infection decreases[16]. Therefore, it is possible for a host to acquire immunity. The immune response of the host may explain the wide variability of host responses to Giardia. Sickness results when the immune system is unable to generate an adequate defense against the protozoan[14]. Previous studies in the area of Giardia immunity have been hampered by the lack of understanding of pathogenic mechanisms.

It has been demonstrated in natural and experimental Giardia lamblia and Giardia muris infections that both cellular and humoral immunity are enerated by the host[1,3,14,17,18]. In natural and experimental infections, development of immunity has been associated with elimination of the parasite[16,19]. However, humans and animals with an elevated immune response to Giardia may still have clinical or subclinical giardiasis which may be due to inadequate immunity in the host[14,20,21]. It has been shown in humans and in animal models that severity of symptoms, course of infection, and infectivity rates are reduced following a second exposure to Giardia parasites[14,16,19].

There have been numerous monoclonal and polyclonal antibodies produced in laboratory animals to Giardia lamblia and Giardia muris trophozoites and cysts. The purposes of producing these antibodies are for diagnostic purposes or reagents for laboratory studies. These antibodies are produced by employing standard hybridoma technology and using BALB/c mice. Polyclonal antibodies have been produced in rabbits and small rodents by performing multiple immunizations with antigens and Freund's adjuvant.

Passive immunization with anti-Giardia antibodies have been conducted. Butscher, et al.[22] demonstrated that intraperitoneal administration of monoclonal antibodies to a surface glycoprotein of G. muris trophozoites reduced parasitic burden in mice. Passive transfer of immunity has been demonstrated in mothers' milk[23]. Mother mice previously infected with Giardia muris were able to confer protection upon their suckling offspring while the milk of naive mothers was not protective.

There are extremely limited studies of active immunization of animals with Giardia trophozoites or with sub-unit vaccines. Roberts-Thomson et al. conducted a study where two strains of laboratory mice were vaccinated and challenged[24]. Intact Giardia muris trophozoites ($10^6$) were combined with Freund's adjuvant (1:1 ratio) and injected intraperitoneally and in the footpad. Four weeks later animals were boosted in the same sites with the same dose without adjuvant. Control mice received only adjuvant or were untreated. One week later mice were challenged with Giardia muris cysts. Vaccinated BALB/c mice had a reduced cyst output for a shorter duration while there was no difference in the cyst output between control and vaccinated C3H/He mice. Thus, this study produced variable and ineffective results.

Vinayak et al.[11] isolated a 56 kDa protein from Giardia lamblia. Mice were subcutaneously immunized (Day 0) and orally immunized (day 7) with 100 µg of multilammelar phosphatidylcholine liposomes (MPL)-entrapped 56 kDa surface associated antigen. Unimmunized and animals similarly immunized with MPL-entrapped PBS (Phosphate buffered saline) served as controls. All animals were challenged seven days after the last immunization dose. Immunization with MPL-entrapped 56 kDa surface-associated antigen resulted in a reduction in trophozoite colonization of the gut and duration of infection when compared to the control groups. It was suggested that the 56 kDa surface antigen immunoregulates the Giardia infection.

It is believed that Giardia secretes cytotoxins that influence the function or structure of the small intestinal mucosa[25,26], but there has yet to be one or more toxic principles identified using classical methods for identification of cytotoxins[25,26]. Culture filtrates of Giardia have been shown to elaborate excretory/secretory products into the culture medium[25]. Culture filtrates have been shown to damage fibroblasts in culture as well as reduce salt and water absorption from perfused loops of rats but the role of these substances in the pathogenesis of giardiasis is unknown[27].

There exists a need for an effective vaccine which can be used to prevent and treat protozoal infections, including giardiasis, in animals, including humans.

SUMMARY OF THE INVENTION

The invention provides vaccines and methods for preventing or treating intestinal protozoal infection in an animal, as well as novel toxins which may be used in said vaccines. Vaccines and methods for preventing or treating giardiasis, in particular, are also provided. The invention also encompasses methods of preparing and methods of use of novel toxins, antibodies, vaccine strains and compositions that result from or are used in these methods.

Accordingly, in one aspect, the invention provides vaccine strains of intestinal protozoa. A method of preparing these vaccine strains is also provided.

Another aspect of the invention is a vaccine composition comprising a vaccine strain of an intestinal protozoan. A cell free vaccine composition comprising a subunit or toxin of an intestinal protozoan is also provided, as is a method of preparing these vaccine compositions.

A further aspect of the invention is a method of preventing or treating infection by intestinal protozoa in an animal comprising administering to the animal an effective amount of a vaccine strain of the intestinal protozoa. A method of preventing or treating infection by an intestinal protozoan comprising administering a cell free composition comprising a subunit or toxin of the intestinal protozoan is also provided.

Yet another aspect of the invention is a toxin of an intestinal protozoan. A method of preparing the toxin is also provided, as are an antibody to the toxin and a method of passive immunization using the antibody.

BRIEF DESCRIPTION OF THE DRAWINGS

FIG. 1. illustrates the growth of various strains of Giardia.

FIG. 2. illustrates the toxin titer of Strain S2 of Giardia in CHO cells.

FIG. 3. illustrates the toxin titer of Strain WB of Giardia in CHO cells.

FIG. 4. illustrates the toxin titer of Strain D3 of Giardia in CHO cells.

FIG. 5. illustrates the effect of vaccination on weight gain in kittens following challenge with Giardia.

FIG. 6. illustrates the effect of vaccination on immune response in kittens.

FIG. 7. illustrates the effect of vaccination on trophozoite count in kittens following challenge with Giardia.

FIG. 8. illustrates the effect of vaccination on the percentage of kitten gut samples in which trophozoites are seen following challenge with Giardia.

FIG. 9. illustrates the excretion of fecal cysts in vaccinated and unvaccinated dogs.

FIG. 10. illustrates the effect of Giardia toxin on CHO cells.

FIG. 11. illustrates a toxin production curve.

FIG. 12. illustrates the effect of bile on the production of Giardia toxin as measured by CHO cell elongation.

DESCRIPTION OF THE INVENTION

A. Definitions

As used herein, the following terms have the following meanings:

Adjuvant: a vehicle used to enhance antigenicity. The use of adjuvants is well-known in the art. Adjuvants may include suspensions of minerals on which antigen may be adsorbed, such as alum, aluminum hydroxide or phosphate; water-in-oil emulsions in which antigen solution is emulsified in mineral oil, such as Freund's incomplete adjuvant; and may include additional factors, such as killed mycobacteria in Freund's complete adjuvant, to further enhance antigenicity.

Antibody: a molecule, especially a protein, that binds immunologically to a known antigen or a determinant of an antigen.

Bile: the substance secreted by the liver and discharged into the duodenum where it aids in the emulsification of fats, increases peristalsis, and retards putrefaction. The term bile is also used to refer to powdered or dried bile. Bile also means any component of bile, such as an individual bile salt.

Colonization: attachment to the gut of the infected animal by the protozoan.

Cyst: the infectious form of many protozoal parasites, such as Giardia. Cysts are usually provided with a highly condensed cytoplasm and resistant cell wall. They are often shed in the feces, and this is the way in which the disease is spread from one animal to another. Cysts may be viable, i.e. able to produce a trophozoite in a new host, or may be non-viable.

Effective Amount: dose required to protect an animal against infection or disease or alleviate a particular symptom of an infection or disease.

Feed Conversion: measure of an animal's ability to gain weight expressed as the weight of feed required to produce a unit quantity of body weight. Intestinal diseases, including those caused by protozoa, reduce this parameter by making an animal less efficient in converting feed to body weight.

Giardia: a genus of parasitic flagellates that parasitize the small intestine. As used in this application, the term includes all species of this genus. The genus Lamblia, formerly used to refer to Giardia, is also included in this term as used in this application.

Giardiasis: infection with Giardia. The symptoms of the infection, such as diarrhea, abdominal cramps, headache, gas, bloat, weight loss, lack of weight gain, dehydration, malaise, malabsorption, colonizing of the gut with the parasite, shedding of cysts, etc. are also included in the term giardiasis.

Immune Response: development in the host of a cellular and/or antibody-mediated immune response to a composition or vaccine of interest. Such a response may consist of one or more of the following: producing antibodies, B cells, helper T cells, suppressor T cells, and/or cytotoxic T cells directed specifically to an antigen or antigens included in the composition or vaccine of interest.

Intestinal Protozoa: any protozoa which inhabits the gut of the animal it infects.

Intestinal Protozoal Infection: infection with an intestinal protozoa. The symptoms of the infection, such as diarrhea, abdominal cramps, headache, gas, bloat, weight loss, lack of weight gain, dehydration, malaise, malabsorption, colonizing of the gut with the parasite, shedding of cysts, etc. are also included.

Neutralize: able to prevent or alleviate toxic effects.

Prevention of symptoms: includes prevention of any effect caused by a toxin.

Production in vitro: production in culture, not in an infected host animal. Production in vitro includes recombinant production.

Protectively Immunogenic: able to protect an animal against infection or disease or alleviate a particular symptom of an infection or disease.

Recombinantly produced: produced by means of gene expression in any other system including microorganisms, plants or animals and/or chemically synthesized by methods known in the art when the sequence is known.

Sonication: disruption of cells by exposing a suspension of the cells to high frequency sound waves.

Subunit: any part of an intestinal protozoa which is less than the whole organism. Subunits that are antigenic may be used in vaccine compositions to produce an immune response. Subunits may include flagella, the ventral adhesive disk, membranes, cytoskeletal membrane proteins, cytosolic membrane proteins, toxins and any other part of an organism which may be antigenic and induce an immune response. This includes recombinantly produced subunits.

Toxin: a noxious or poisonous substance that is produced by an intestinal protozoa. It may be an extracellular product (exotoxin). When intestinal cells are affected, a toxin is classified as an enterotoxin. This includes recombinantly produced toxins.

Trophozoite: the vegetative form of certain intestinal parasites, such as Giardia.

Vaccine Strain: a strain of an intestinal protozoa which is protectively immunogenic when administered to an animal. This includes strains which have been genetically attenuated.

B. Detailed Description of The Invention

This invention provides vaccine strains of intestinal protozoa and toxins from said protozoa. It has unexpectedly been found that culturing intestinal protozoa in media containing bile makes them protectively immunogenic when used to vaccinate animals. Further, said culture in bile-containing media provides for production, in vitro, of a toxin. This toxin may be used for immunization against infection by the intestinal protozoa or for raising toxin-neutralizing antibodies.

In particular, intestinal protozoa which are present extracellularly in the gut of the host animal are preferred for use in the present invention. In a most preferred embodiment, the invention provides vaccines strains, toxins, and antibodies to toxins of Giardia. Such strains, toxins and antibodies are useful for preventing and treating giardiasis and the symptoms thereof.

A variety of Giardia strains are useful in the present invention. Strains which grow well in vitro, are able to infect target animal species, and produce a toxin when grown in vitro are preferred. In particular, Giardia strains WB (a human isolate), S2 (a strain which we isolated from sheep), D3 (a strain which we isolated from dogs), and N (a strain which we isolated from drinking water) may be used. Strains S2 and D3 are most preferred.

The Giardia strains of this invention were cultured by growing them in TYI-S-33 media containing bile. Dehydrated bovine bile was generally used, however it is anticipated that fractions of bile, including individual bile salts, will be useful in the present invention. The Giardia trophozoites may be grown in containers which also contain finely divided solid supports. This increases the surface area to which the trophozoites may attach. Dextran beads are a particularly preferred solid support[29]. Other support systems such as glass beads or fibers may also be suitable. Details of media preparation, Giardia trophozoite subculture and harvest are set forth in the Examples below.

The invention also provides vaccine compositions comprising a vaccine strain of Giardia or other intestinal protozoa which is effectively immunogenic. Various strains of Giardia may be useful in such vaccine compositions. In particular, strains which produce a toxin when cultured in vitro are preferred. Examples of most preferred strains are Giardia strains S2 and D3.

The vaccine strains may be cultured as set forth in the Examples below, then harvested for use in vaccine compositions. Protozoa may be disrupted before use in vaccine compositions. Various methods of disruption may preferably be used, including sonication, osmosis, the use of pressure differentials, or freezing. Sonication is most preferred.

Vaccine compositions may contain one or more vaccine strains of an intestinal protozoan and/or one or more subunits and/or toxins of Giardia or other intestinal protozoa. Such subunits and/or toxins may be used in addition to whole or sonicated protozoa or may be used in cell-free vaccine compositions.

It may be useful to inactivate the intestinal protozoa, toxins or subunits before use in vaccine compositions. Conventional techniques such as mild heat treatment or formalin inactivation may be used.

The formulation of such vaccine compositions may include suitable pharmaceutical carriers, including adjuvants. The use of an adjuvant, such as an alum-based adjuvant, is preferred. Many commercial adjuvants would be useful in the present invention. For these studies, an alum-based adjuvant containing aluminum hydroxide and Quill A (Super Fos, Copenhagen, Denmark), was used. Exact formulation of said vaccine compositions will depend on the particular vaccine strain, the species to be immunized and the route of immunization. Such vaccine composition formulation is well-known to those skilled in the art.

Such vaccine compositions are useful for immunizing any animal susceptible to intestinal protozoa, such as bovine, ovine, caprine, equine, leporine, porcine, canine, feline and avian species. Both domestic and wild animals may be immunized, and immunization of food producing animals is contemplated. Humans, may also be immunized with these vaccine compositions.

The present invention provides a method of preventing or treating giardiasis or other intestinal protozoal infection by administering an effective amount of a vaccine strain of Giardia or other intestinal protozoa to an animal in need of such prevention or treatment. Such vaccine strain may be used in a vaccine composition as previously discussed. This method is useful in dogs, cats, humans, domestic animals (especially food producing animals), avian species, and wild animals. Use in wild animals may prevent contamination of water supplies used by humans or domestic animals.

The route of administration may be any convenient route, and may vary depending on the intestinal protozoan, the animal to be treated, and other factors. Parenteral administration, such as subcutaneous, intramuscular, or intravenous administration, is preferred. Subcutaneous administration is most preferred for canine and feline species. Oral administration may also be used, including oral dosage forms which are enteric coated.

The schedule of administration may vary depending on the intestinal protozoa and the animal to be treated. Animals may receive a single dose, or may receive a booster dose or doses. Annual boosters may be used for continued protection. In particular, two doses 21 days apart are preferred as a primary course.

The age of the animal to be treated may also affect the route and schedule of administration. Administration is preferred at the age when maternal antibodies are no longer present and the animal is immunologically competent. This is about 6 to 7 weeks of age in canine or feline species. Additionally, immunization of mothers to prevent infection of their offspring through passive transfer of antibodies in their milk is preferred.

The method of this invention is effective in preventing colonization of the gut, i.e. preventing attachment of the protozoa to the gut mucosa. It is also effective in preventing symptoms of giardiasis. This includes neutralizations of toxin and prevention of any physiological toxin effects which may occur when the organisms may be present in the lumen of the gut, but not attached. Further, the method of this invention decreases fecal shedding of cysts, and in particular, viable cysts. This prevents further spread of infection.

Treatment may be administered to symptomatic or asymptomatic animals, including animals or humans with chronic infection, and may be used to increase growth rate by alleviating such symptoms of infection as diarrhea. Thus, when administered to a food producing animal, it may increase feed conversion.

The present invention provides toxins of Giardia or other intestinal protozoa and methods of producing these toxins. It has unexpectedly been found that culturing organisms in media containing bile causes them to produce a toxin in vitro. This toxin may be used to immunize animals against intestinal protozoal infection. When the media in which these organisms were grown was concentrated, a toxin useful for preventing and/or treating infection was obtained. This toxin in Giardia is an exotoxin and highly cytotoxic. It appears to be a potent enterotoxin.

Until recently, attempts to isolate a Giardia enterotoxin had been unsuccessful. But the use of concentrated solutions and a more sensitive assay system has allowed the detection of a cytotoxic factor that is produced by Giardia. The toxin was detected using Chinese Hamster Ovary (CHO) cells. The CHO bioassay has been determined to be 100–10,000 times more sensitive than skin permeability, fat cell lipolysis and ileal loop assays. Tests with the toxin have shown it to cause CHO cell elongation. The amount of elongation (i.e. the percentage of cells elongated) was found to generally increase with toxin concentration. The results observed with the Giardia toxin are very similar to other work done with bacterial enterotoxins. A similar effect on CHO cells has been found using *E. coli* toxins, cholera toxin, and pertussis toxin.

Partial purification of the Giardia toxin has been achieved. It has been established that the Giardia toxin is an intracellularly produced protein which is stable at 37° C., at room temperature, when refrigerated, or when frozen. Using SDS-PAGE, it has been established that media containing toxin contains Coomassie-staining proteins of approximate molecular weight of 22, 32, 38 and 39 kDa, as well as several proteins of molecular weight greater than 97 kDa, which are not present in control media.

Immunization with the toxin reduced symptoms of giardiasis, including diarrhea and decreased fecal cyst shedding.

The present invention also provides antibodies to toxins of Giardia or other intestinal protozoa. Polyclonal antibodies have been raised to Giardia toxin. Monoclonal antibodies may also be raised by conventional techniques. These antibodies will be useful as an antiserum to neutralize the toxic effects of the toxin. Thus, they may be expected to relieve symptoms of giardiasis or other intestinal protozoal infection. It is expected that oral administration of these antibodies using an enteric coated dosage formulation will be preferred.

The methods of this invention will be useful to produce vaccine strains, vaccine compositions, toxins, and antitoxins for preventing and treating other intestinal protozoal infections. Other intestinal protozoa useful in the present invention include cryptosporidium, trichomonads, histomonas, spironucleus, entamoeba, coccidia, toxoplasma and sarcocystis. In particular, cryptosporidium, trichomonads, histomonas, spironucleus and entamoeba are preferred.

*Cryptosporidium muris* (also called *Cryptosporidium parvum*) is a protozoan parasite found in the small and large intestine of mammals and poultry and *Cryptosporidium melegridis* is found in the brush border of the respiratory and gastrointestinal tract of poultry. The parasite causes mild to severe diarrhea in humans, other mammals and birds, and respiratory disease in birds. Cryptosporidium causes a reduction in brush border surface area, impaired electrolyte transport and a malabsorptive diarrhea similar to giardiasis. There is a tremendous potential for the development of a whole cell or subunit vaccine for Cryptosporidium spp. This vaccine can be prepared by disrupting the parasite, combining these proteins with adjuvant and immunizing animals or humans by an oral or a parenteral route. One or more toxins may be an important virulence factor and these toxins (or toxoids) can also be used to vaccinate by oral or parenteral routes. The vaccine may be used to prevent the disease or protect against the symptoms of the disease. Anti-toxin antibodies may be used to treat the symptoms of cryptosporidiosis.

Trichomonads are a large family of flagellated protozoan parasites which are found in the gastrointestinal, reproductive and respiratory tracts of mammals and birds. Most trichomonads are believed to be non-pathogenic commensals. However, we believe that like Giardia, some of these protozoan parasites may influence weight gain and feed conversion in animals and in some cases may cause diarrhea. The mechanism may be toxin mediated. Vaccination with disrupted trichomonas parasites and adjuvant may provide protection from infections or reduce symptoms of the infection. Similarly a toxin or toxoid may provide protection. The vaccine would prevent colonization of the gut and the injury to the gut. There may be cross protection of different trichomonad species.

*Histomonas meleagridis* is a flagellated protozoan parasite of poultry. The parasite is released from the cecum and passes by way of the blood stream to the liver. There is necrosis and tissue degeneration of the liver and cecum. Birds that have recovered from the infection are immune to the disease. We believe a toxin may be involved in the pathogenesis of the disease. Vaccination with a disrupted cell or toxin vaccine may provide an effective method of control of histomoniasis in poultry. The vaccine would prevent colonization of the gut or penetration of the cecum. The vaccine may also prevent the necrosis of the liver and cecum.

*Spironucleus meleagridis* is a disease of young birds resulting in diarrhea and death. The gut is found filled with a watery fluid on post mortem. This parasite infects domestic and wild birds. We believe that *Spironucleus meleagridis* induces symptoms through a toxin mediated process. A disrupted whole parasite or toxin or toxoid vaccine may provide protection from this infection. The vaccine would neutralize the toxin and/or prevent colonization of the parasite.

*Entamoeba histolytica* is a pathogenic amoebic protozoan which causes amoebic dysentery in humans and animals. The organism colonizes the cecum and colon causing diarrhea and dysentery. The parasite may invade the gut wall and multiply in the submucosa causing ulceration. The parasite may also enter the lymph ducts or mesenteric veins resulting in abscesses throughout the body. We believe that one or more toxins may be important virulence factors. Vaccination using disrupted trophozoites and/or toxin may act to provide protection against colonization and/or invasion of the parasite. Vaccination may also protect against the diarrhea and dysentery seen in this disease, as it would neutralize the toxin and/or prevent invasion of the parasite.

Coccidiosis is a complex intestinal disease induced by Eimeria spp. or Isospora spp. and is of major economic importance in domestic animals. These protozoans have a complex life cycle and are host specific. Attempts to produce vaccines have been made. Poultry vaccines have been produced (CocciVac, CocciVacT, Sherwin Laboratories). These vaccines include all the pathogenic species for chicken and turkeys. Development of subunit vaccines have been largely unsuccessful. A coccidia toxin has not been identified and toxin vaccines have not been produced. There is a potential to produce a subunit or fortified vaccine based on a toxin or toxoid for coccidia of humans and animals. These include: Isospora spp., Eimeria spp., Wenyonella spp. and Tyzzeria spp.

Toxoplasma have a complex life cycle. Several investigative groups have been unable to protect mice, hamsters and rabbits by experimental immunization with heat-killed and heat- or formalin- killed homologous tachyzoites, with or without adjuvant. Certain fractions have provided protection against experimental challenge. A cytotoxin of Toxoplasma has not been identified; however, immunization with a toxin or toxoid may provide protection from this disease in animals and humans.

Like coccidia, Sarcocystis have a complex life cycle with the oocysts being present in the predators' intestinal cells and during the asexual stage in the tissues of the prey animal. They are common in many domestic and wild animals. At the present time there is no vaccine for these protozoan parasites and a cytotoxin has not been demonstrated. There is potential for vaccine development for this parasite using the present invention.

The following examples are not intended to limit the scope of the invention in any manner.

C. Examples of Embodiments of The Invention

In general, the following materials and methods were used in these examples unless otherwise noted:

1. Media recipe and preparation

Media for *G. lamblia* (TYI-S-33) was prepared using the following ingredients.

|  | g/l |
|---|---|
| Casein Hydrolysate (Gibco 152-0014M) | 20.0 |
| Yeast Extract (BBL 11929) | 10.0 |
| Dextrose (anhyd.) | 10.0 |
| NaCl | 2.0 |
| $K_2HPO_4$ (anhyd.) | 1.0 |
| $KH_2PO_4$ (anhyd.) | 0.6 |
| L-Cysteine (Sigma C 2529) | 2.0 |
| L-Ascorbic Acid (Sigma A 4034) | 0.2 |
| Bovine Bile (Sigma B 3883) | 0.8 |

Chemicals were from British Drug Houses (BDH) unless otherwise specified.

The above dry ingredients were combined and stored in the dark at 4° C. until needed. National Collection of Type Cultures, Colindale, England, (NCTC) vitamin mix (Gibco Cat. #440-1100 EB) was prepared according to package instructions, sterile filtered (0.22μ) and stored as 30 ml aliquots at −20° C. A solution of ferric ammonium citrate was prepared by suspending 2.28 g in 50 ml distilled water ($dH_2O$) using a volumetric flask. The solution was stored in the dark at 4° C., as it is photolabile. CLEX (Fetal Calf Serum (FCS) substitute) was thawed, then stored at −20° C. as sterile 100 ml aliquots (Dextran Products CLEX C-500).

For one liter of media, half of 870 ml $dH_2O$ was poured into a 1L flask with stirring bar, dry ingredients were added, and the remaining water used to rinse the container and flask edges. Then 500 ml of the ferric ammonium citrate solution was added. The solution was stirred until the media was transparent (usually 2–3 hours), then the pH adjusted to 6.8 with 5M NaOH. The media was sterile filtered (0.22μ and prefilter) under aseptic conditions, 30 ml of vitamin mix and 100 ml of CLEX added and mixed. Prepared media was aliquoted and stored at −20° C. until needed.

2. Freezing Giardia trophozoites

Giardia trophozoites were frozen using the following procedures. Giardia were grown into late log phase (72 hours). Media was poured out so as to retain the healthy trophozoites which were on the sides of the tube. Fresh media was poured in, and the tubes cold shocked on ice for 10–15 minutes, then centrifuged at 500 xg for 10 minutes at 4° C. Under sterile conditions, 14 ml of media was pipetted off, leaving approximately 2 ml for resuspension of the trophozoites. About 0.9 ml of this trophozoite suspension was added to cryotubes containing 0.9 ml of 20% DMSO in CLEX. The cryotubes were placed into canes for storage in liquid $N_2$ and placed in an insulated container. The insulated container was placed into a −70° C. freezer for a minimum of 12 hours and a maximum of 72 hours, then into the liquid $N_2$ freezer.

Trophozoites were quick thawed by placing cryotubes into a 37° C. water bath, placed into fresh media and incubated horizontally for the first day, subcultured after 24 hours and incubated as usual.

3. Subculturing Giardia trophozoites

The *Giardia lamblia* strains used were: WB (a human isolate, ATCC 30957), S2 (a strain isolated from sheep in our laboratory), D3 (a strain isolated from dogs in our laboratory), and N (a strain isolated from drinking water from Botwood, Newfoundland in our laboratory).

The procedures following were used to subculture Giardia trophozoites of all strains used. Giardia were grown into late log phase (72 hrs), then cold shocked by placing culture tubes into ice for 10 to 15 minutes. Under a laminar flow hood, approximately 7–8 mg of Piperacillin (Pipracil, Lederle) was added to each new culture tube, then 15 ml of fresh TYI-S-33 media was added to each new tube. After cold shocking, tubes with late log Giardia were inverted a few times to mix up the settled and adherent populations. With a sterile 1 ml pipette, 1 ml of trophozoites was removed and added to the new culture tube, flushing the pipette 1 to 2 times. New tubes were sealed with Parafilm and placed upright in a 37° C. incubator. Subculture was done again in 3 to 4 days.

Alternatively, Giardia trophozoites were cultured in double surface glass roller bottles (Bellco Cat. #7730-38910). Concentrations of $10^6$ trophozoites per ml culture medium are easily obtained after 72 hours of incubation. Each roller bottle required approximately 650 ml of media. In order that the bottle be full enough to extrude any large air bubbles, the media was warmed to 37° C. before use. To avoid exposing trophozoites to a high concentration of Piperacillin at the top of the bottle, the antibiotic was first dissolved in some media (to approximately 0.5 mg/ml final concentration), the solution poured into the bottle, the bottle filled to near the top with more media, Giardia added (a minimum of $10^6$ trophozoites, cold shocked as above), the bottle filled to the top, any air bubbles removed using a pipette, and the bottle tightly sealed with Parafilm. The roller bottle apparatus (Wheaton Model III) was set to 6–8% of motor output (two revolutions per minute) and bottles cultured for 3–4 days.

4. Harvesting Giardia trophozoites

Giardia trophozoites were harvested as follows. Giardia were grown into late log phase (72 hrs), then cold shocked by placing tubes or bottles on ice (15–20 minutes for 10 and 30 ml tubes, 45 minutes for roller bottles). Tubes or bottles were then inverted several times, and the contents poured into sterile centrifuge tubes or bottles. These were spun at 500×g, at 4° C. for 10 minutes, to pellet the trophozoites. Media was removed and the pellet resuspended in sterile PBS (pH 7.2) to the original volume of the media. The suspension was spun at 500×g, 4° C., for 10 minutes. Supernatant was removed and the trophozoites resuspended in fresh PBS. A total of four PBS washes was performed. After the final spin, the trophozoites were resuspended to the desired concentration in PBS.

The trophozoites were centrifuged at low speed so as not to damage them, thus the pellet formed is very soft and the organisms are motile. It is important to move quickly to remove the supernatant before the pellet resuspends itself.

5. Sonicating Giardia trophozoites

Giardia trophozoites were sonicated using a Virsonic Cell Disrupter. Three 20 second bursts were generally sufficient. The presence of intact trophozoites was checked using a hemocytometer. An additional burst was used where necessary for complete disruption. Trophozoites were kept on ice at all times, and the sonicator tip cooled with 70% ethanol between bursts. Sonicates were aliquoted and stored at −20° C.

6. Preparing whole sonicate vaccine

Whole sonicate vaccine of Giardia was prepared as follows. The protein concentration of the sonicate was determined (BIORAD Protein Assay) and adjusted to 0.75 mg/ml in sterile PBS. This solution was mixed 4:1 with the previously described alum-based adjuvant for use in immunizing animals in the following studies.

7. Concentrating Giardia toxin.

Giardia medium and very dilute samples were concentrated to achieve a useful concentration of toxin using an Amicon apparatus (Model No. 8200). This device uses $N_2$ pressure to force water and low molecular weight (MW) particles through a membrane with a specified MW cutoff. The membrane YM-10, used for these studies, has a MW cutoff of 10,000. The apparatus also contains a stir bar which helps to keep proteins from plugging the membrane, allowing water to pass through more easily.

Membranes were sometimes used more than once for the same protein. After use, the membrane was rinsed in $dH_2O$ and refrigerated in 10% ethanol. New membranes were soaked in $dH_2O$ for 1 hour with three water changes to remove the membrane preservative.

8. Young kitten model

An investigation into the feasibility of using young (6–8 week) kittens as a model infection system was performed as our initial study. Multiple fecal flotations were performed on feces of these kittens during their conditioning period to ensure giardia-free status. Kittens (n=6) were anesthetized, laparotomies were performed and the kittens were inoculated intraduodenally with $1.0 \times 10^6$ Giardia lamblia trophozoites in 1.0 ml PBS. Each of two kittens received the following Giardia lamblia strains: 1) WB strain (a well characterized human isolate, ATCC 30957); 2) S2 strain (a strain isolated from a sheep by our laboratory); or 3) D3 strain (a strain isolated from a dog by our laboratory).

Clinical signs were monitored and four fecal examinations for cysts performed during the 7 days immediately following infection (see Table 1). Serum samples were taken on the day of experimental infection and the 7th day (the day of post mortem) for determination of IgM titer and IgG titer (Table 2) to the respective sonicated Giardia strains (i.e. WB, S2, D3 respectively). Trophozoite counts were performed on 1.0 cm lengths of duodenum from each kitten (Table 3) and tissue samples taken for light microscopy and electron microscopy. Bile and mucosal scrapings were collected and stored frozen (−70° C.) for future local immunological response testing and enzymatic assays.

Protozoan parasites with morphology typical of Giardia lamblia were seen in the duodenum, jejunum and (to a lesser extent) ileum of WB and S2 infected kittens. No trophozoites were evident in D3 infected kittens using any of the microscopy techniques. Based on this pilot investigation, it was decided to use the kitten infection model for further studies, since Giardia strains are infective and produce clinical signs in this model.

TABLE 1

Clinical Signs of Giardia Infected Kittens

| KITTEN NUMBER | Giardia STRAIN | SYMPTOM PRESENT | FECAL RESULT FOR GIARDIA |
|---|---|---|---|
| 1 | WB | SOFT STOOL | NEGATIVE |
| 2 | WB | SOFT STOOL | NEGATIVE |
| 3 | S2 | DIARRHEA | POSITIVE |
| 4 | S2 | SOFT STOOL | POSITIVE |
| 5 | D3 | DIARRHEA | NEGATIVE |
| 6 | D3 | SOFT STOOL | NEGATIVE |

TABLE 2

Kitten Serum ELISA Titers to Giardia

| KITTEN NUMBER | Giardia STRAIN | DAY 0 TITER | | DAY 7 TITER | |
|---|---|---|---|---|---|
| | | IgM | IgG | IgM | IgG |
| 1 | WB | 8 | 1 | 8 | 256 |
| 2 | WB | 16 | 0 | 16 | 16 |
| 3 | S2 | 64 | 4 | 64 | 128 |
| 4 | S2 | 64 | 0 | 64 | 64 |
| 5 | D3 | 64 | 2 | 32 | 640 |
| 6 | D3 | 32 | 4 | 32 | 256 |

TABLE 3

Duodenal Tissue Trophozoite Counts

| KITTEN NUMBER | Giardia STRAIN | TROPHOZOITE COUNT |
|---|---|---|
| 1 | WB | $8.75 \times 10^3$ |
| 2 | WB | $5.0 \times 10^3$ |
| 3 | S2 | 0 |
| 4 | S2 | $2.0 \times 10^4$ |
| 5 | D3 | 0 |
| 6 | D3 | 0 |

9. Enzyme linked immunosorbent assay (ELISA)

Cat and dog gut mucosal homogenate samples were prepared by homogenizing tissue at 10% weight per volume in 2 mM EDTA, then stored at −80° C. Samples were thawed, diluted 1:2 (cat) or 1:1 (dog) with PEPBS (2 mM EDTA, 1 mM PMSF), the mixture dispersed by five passes through an 18G needle, then spun at 17,000× g for 20 minutes. The supernatants, which contained soluble protein fractions, were used to perform the ELISA. Serum and bile samples were stored at −80° C., thawed, diluted 2-fold with PEPBS, centrifuged, and supernatants removed for use in performing the ELISA. All samples were assayed in duplicate.

Blocking for all assays other than dog IgG serum assays was done with 2% gamma globulin-free FCS in PBS for one hour at 37° C. with 3 washes. Dog IgG serum assays were blocked with 10% skim milk powder in PBS for one hour at 37° C.

For cat IgG assays, sonicated Giardia (S2) was used as the antigen. Sonicated S2 (0.2 mg/ml in PBS) was added to each well (100 µl per well) and incubated at 4° C. overnight. The wells were then washed (3 times) with PBS-tween. Serum, bile or gut mucosal supernatants prepared as previously described were used as the primary antibody (37° C., 1 hour, 3 washes). Goat anti-cat IgG-HRP (KPL cat. #042002) diluted 1:1000 in PBS was used as the secondary antibody (37° C., 1 hour, 4 washes).

For IgA cat assays, sonicated Giardia S2 strain was used as the antigen. Serum bile or gut mucosal supernatants prepared as previously described were used as the primary antibody. Goat anti-cat IgA (Bethyl Lab. cat #A20-101) diluted 1:250 in PBS was used as the secondary antibody (37° C., 1 hour, 4 washes). Rabbit anti-goat IgA-HRP (Sigma cat. #A-4174) diluted 1:500 in PBS (37° C., 1 hour, 4 washes) was used as the tertiary antibody.

For dog assays, sonicated Giardia S2 strain was used to coat the well as described in the cat assay. Serum bile or gut mucosal supernatants prepared as previously described were used as the primary antibody. Goat anti-dog IgG-HRP (KPL cat #041902) or goat anti-dog IgA-HRP(Bethyl Lab. Cat. #A40-104P) diluted 1:1000 in PBS was used as the secondary antibody.

EXAMPLE 1

Strain Selection and Preservation

A variety of strains of Giardia lamblia were grown in vitro in tubes of TYI-S-33 medium using our standard laboratory methodology. Primary and secondary stocks were stored frozen at-70° C. Growth curves of these three strains of Giardia lamblia (WB, S2, D3) have been determined (FIG. 1) and compared to toxin response (cell elongation) of Chinese Hamster Ovary (CHO) cells (FIGS. 2–4). Although D3 showed the most impressive growth characteristics, all three strains appeared promising based on adequate growth abilities in vitro, ability to infect target animal species, and toxic effects on CHO cells.

EXAMPLE 2

Kitten Vaccination—Experimental Infection

For this investigation, the following experimental groups were established: Group A - 7 kittens were sham-immunized with 0.2 ml of the previously described adjuvant and 0.8 ml PBS administered subcutaneously, then infected with Giardia lamblia strain S2 by intraduodenal inoculation of $1 \times 10^6$ viable trophozoites in 1.0 ml PBS on day 28; Group B - 3 kittens were vaccinated with 0.2 ml adjuvant and 0.8 ml concentrated (10×) culture supernatant of S2 (750 µg protein/ml and demonstrated CHO cell toxic activity) administered subcutaneously, boosted with the same preparation on day 21, then infected with S2 intraduodenally on day 28; Group C - 8 kittens were vaccinated with 0.2 ml adjuvant and 0.8 ml sonicated whole S2 trophozoites (750 µg protein/ml) administered subcutaneously, boosted with the same preparation on day 21, then infected intraduodenally with S2 on day 28.

Clinical signs were monitored and quantitative fecal cyst counts were performed daily for 42 days following infection. The kittens were weighed daily and growth curves generated for the non-vaccinated group (Group A) and the S2 sonicate vaccine group (Group C). Serum samples were obtained weekly and at post mortem for IgG ELISA titers. After euthanasia, gut samples (duodenum, jejunum, ileum) were taken for trophozoite counts, light microscopy, and electron microscopy. Mucosal scrapings, serum samples and bile were collected and stored frozen (−70° C.) for immunological analyses and enzymatic investigations.

Intermittent diarrhea or soft stools were seen irregularly in all kittens in this study. No differentiation of severity was observed between non-vaccinated animals and vaccinated animals. The weight gain data for the non-vaccinated Group A and sonicated S2 vaccinated Group C after infection with Giardia lamblia are shown in FIG. 5. Vaccinated kittens gained significantly more weight during the study than non-vaccinated controls. Immunological responses in kittens of these 3 experimental groups, as determined by serum IgG ELISA, are shown in FIG. 6. Both Group B (toxin immunized) and Group C (sonicated S2-immunized) showed a significant increase in serum IgG, a typical response to immunization and boosting. Only a minimal increase in titer was seen in these immunized animals post-infection with Giardia. In contrast, the Group A or non-immunized infected kittens showed a response only after infection, but this was a minimal increase in serum titer. Also included in FIG. 6 are the IgG titers of a single (n=1) non-immunized and non-infected kitten. Intestinal trophozoite counts were performed on 1.0 cm gut segments from the duodenum, jejunum and ileum of all kittens. The results are illustrated in FIG. 7. Immunization with sonicated S2 trophozoites (Group C) reduced the number of trophozoites present in the gut lumen of the duodenum and jejunum when compared to non-vaccinated kittens (Group A). Data from toxin-immunized (Group B) animals is less convincing, possibly due to the comparatively smaller "n" value (n=3) of this group. Alternatively, immunization with toxin alone may prevent symptoms but not infection, or a higher dose of toxin may be more effective. Interestingly, trophozoites were not readily found in the ileum as has been typically described for giardiasis in domestic cats[30]. A variation of the intestinal trophozoite data described above is also shown in FIG. 8, where the percentage of gut samples in which trophozoites were seen are compared among experimental groups. A comparatively small percentage of gut samples were positive for the presence of Giardia trophozoites in the sonicated S2 immunized (Group C) kittens when compared to non-immunized (Group A) and toxin-immunized (Group B) kittens.

Immunization with sonicated S2 trophozoites reduced the severity of cyst excretion in kittens.

Microscopic examination of select intestinal tissue samples indicated that trophozoites were present in non-immunized kittens but not present or infrequently observed in sonicated S2-immunized kittens.

The results of immunological studies of IgA levels in serum and gut mucosa are presented in Table 4. No IgA response was noted in unvaccinated, unchallenged animals. A strong IgA response was noted in animals vaccinated with S2 sonicate and challenged. In contrast, non-vaccinated challenged animals showed only a weak IgA response. There was a moderate IgA response in toxin vaccinated and challenged animals. Thus, vaccination induced a stronger IgA immune response than natural infection. A nonspecific immune response was noted in all bile samples, including in non-vaccinated, non-challenged animals.

TABLE 4

Serum and Mucosal Antibody IgA Titers

| Group | Cat No. | Serum | Duodenum | Jejunum | Ileum |
|---|---|---|---|---|---|
| Non-Vaccinated and not challenged | 1 | 0 | 0 | 0 | 0 |
| Non-Vaccinated and challenged | 2 | 80 | 80 | 10 | 20 |
|  | 3 | 40 | 40 | 20 | 40 |
| Vaccinated with toxin and Challenged | 4 | 800 | 40 | 80 | 20 |
|  | 5 | 120 | 40 | 0 | 10 |
|  | 6 | 600 | 40 | 80 | 80 |
| Vaccinated with S2 Sonicate and Challenged | 7 | 4,000 | 160 | 160 | 80 |
|  | 8 | 800 | 80 | 80 | 40 |
|  | 9 | 1,200 | 80 | 80 | 20 |
|  | 10 | 4,000 | 320 | 40 | 320 |
|  | 11 | 1,000 | 160 | 160 | 160 |
|  | 12 | 2,000 | 640 | 160 | 160 |
|  | 13 | 2,000 | 80 | 160 | 320 |
|  | 14 | 3,200 | 320 | 160 | 640 |

EXAMPLE 3

Dog Vaccination—Experimental Infection

A study of the efficiency of vaccination with sonicated Giardia strain S2 in dogs was performed as follows: Two groups of four puppies, 8 to 10 weeks of age, were used. One group of animals (numbers 1 to 4) received, subcutaneously, a vaccine containing sonicated Giardia strain S2 prepared as described previously (day 1). Each animal received 1 ml of vaccine containing 600 μg protein in 0.8 ml PBS and 0.2 ml of the previously described adjuvant. The other group (numbers 5 to 8) was not vaccinated.

Three weeks later (day 21), animals 1 to 4 received a booster vaccination of the Giardia vaccine as above. Animals 5 to 8 were not vaccinated. On day 28, all pups were challenged with $4 \times 10^6$ Giardia lamblia strain N trophozoites. Strain N was used because it is highly infective in dogs. The challenge organisms were administered intraduodenally in 1.0 ml PBS. Results show that immunization with Giardia strain S2 is cross protective against infection with Giardia strain N.

Following challenge, blood samples were collected weekly, feces were examined daily for consistency, and cyst shedding until sacrifice of all animals on day 56.

Vaccination protected dogs against diarrhea, with vaccinated animals having diarrhea for a mean of only 2.2±1.5 days while unvaccinated animals exhibited diarrhea for a mean of 8.2±5.6 days.

Cyst output data showed that vaccinated animals shed fewer cysts than unvaccinated animals. Results are shown in FIG. 9.

Gut segments 1 cm in length were suspended in PBS and shaken for one hour at 37° C. The number of trophozoites were counted on a hemocytometer. Results are shown in Table 5. Vaccination eliminated Giardia trophozoites from all areas of the intestine of immunized animals.

TABLE 5

Trophozoite Counts per cm Intestine

| | Immunized | | | Non-immunized | | |
|---|---|---|---|---|---|---|
| | Duodenum | Jejunum | Ileum | Duodenum | Jejunum | Ileum |
| Mean | 0 | 0 | 0 | 0 | 30000 | 313 |
| SD | 0 | 0 | 0 | 0 | 44200 | 625 |
| SE | 0 | 0 | 0 | 0 | 22100 | 313 |

The vaccine induced a specific serum and mucosal immune response to Giardia. There was a strong serum IgG response to the vaccine starting three weeks after vaccination. In contrast, unvaccinated dogs had a weak response only after four weeks of infection.

There was a weak to moderate serum IgA response after vaccination and challenge in week six, but no serum IgA response in unvaccinated animals. Both groups had detectable IgA in the bile at post mortem. IgA was detected in the duodenum and ileum in vaccinated and unvaccinated animals.

Example 5

Production, Purification and Assay of Toxin

The WB isolate of Giardia lamblia was cultured at 37° C. for 10 days in TYI-S-33 media supplemented with NCTC-109 vitamin mix (3%), CLEX (10%), bile (0.8 g/l) and Piperacillin. Cultures were maintained in log phase with transfers at 3 day intervals. After 10 days, the medium was centrifuged at 3,000×g for 15 minutes, sterile filtered (0.22 μ filter—Nalgene Co.) and concentrated with an Amicon apparatus with YM-10 membrane filter.

The Chinese Hamster Ovary cell line CHO-K1 (ATCC No. CCL61) was grown in Eagles' alpha minimal essential medium (MEM) supplemented with 10% fetal calf serum (FCS) and 0.5% penicillin and streptomycin with amino acids in 5% $CO_2$ at 37° C. with 90% relative humidity.

For morphological studies, a suspension of $5 \times 10^3$ CHO cells in 200 μl of media was added to each well of a 96 well tissue culture plate (Linbro Corp.) and incubated in 5% $CO_2$ at 37° C. for 48 hours. The medium in each well was collected with a pipette and replaced with 150 μl of fresh medium. Fifty μl of the substance to be tested was added to the first well of a row and a serial four-fold dilution was performed to the end of the row (12 wells). The plate was again incubated for 48 hours. Each well was then stained with Giemsa stain and the percentage of elongated cells was determined. Each morphological datum on the graph represents the mean percentage of cells elongated from 500 cells counted (FIG. 10). Results of assay of Giardia lamblia concentrated medium were compared to a control of concentrated Giardia-free medium. Cholera toxin (Sigma Corp.) and pertussis toxin were used as positive controls. Cholera toxin elicits a characteristic elongation reaction and pertussis toxin elicits a characteristic clumping reaction.

The effect of varying dilutions of the filtrates on the morphology of CHO cells is illustrated in FIG. 10. The elongation of the cells is striking after exposure to concentrated Giardia 10 day media (GM). CHO cells also displayed elongation, but not to the same degree, when exposed to an identical dilution of concentrated control sterile medium (CM). The CM showed some morphological response at the higher concentrations, but even the greatest response resulted in elongation of only 31.6% of CHO cells at a concentration of 0.25× original conc. The GM had a much greater effect on CHO cell morphology at the higher concentration (75% at 0.25× original conc.) and also produced elongation at very low concentrations. Elongation of CHO cells resulted at concentrations above $1.5\times10^{-5}\times$ the original concentrated Giardia media. The elongation produced by the GM increased after the first dilution and then began to decrease with subsequent dilutions (FIG. 10).

Five hundred thousand trophozoites were inoculated at day 0 into 16.0 ml of fresh TYI-S-33 medium in 10 culture tubes. Trophozoites were counted daily from one tube randomly selected. A 2.0 ml sample of the medium was withdrawn and sterile filtered with a 0.22 µ filter (Costar Corp.). One ml of the sterilized culture medium was refrigerated at 4° C. and the other 1.0 ml was frozen at −70° C. This procedure was repeated for eight days. Each fraction of culture medium collected was assayed as described above with the CHO cell bioassay.

Healthy log phase Giardia trophozoites were washed twice in 20 mM Tris buffer, pH 6.0, centrifuged for 15 min. at 5,000× g, then resuspended in 1.0 ml of buffer. The trophozoites were then sonicated by one 15 sec. burst and the sonicate examined by light microscopy for surviving trophozoites. The sonicate was filtered through a 0.22 µ filter (Costar Corp.) to collect the cytosolic contents. The filter was backwashed with 1.0 ml of buffer to collect the membranes and cytoskeletal fractions. The buffer, the cytosolic fraction, and the membrane fraction were assayed for toxic activity with the CHO cell bioassay.

The growth media (GM) titer and Giardia growth curve relationship is depicted in FIG. 11. The Giardia trophozoites divide and increase in number in a logarithmic fashion. There is a lag phase evident on day one, an acceleration phase on day two, a deceleration phase on day three. Thereafter, the trophozoite number declines steadily. The trophozoites reached a maximum number of $4\times10^7$ at day three. The titer of the media began to increase after day one and increase during the growth phase of the trophozoites. After day three, when the trophozoite number began to decline, the titer continued to increase.

Proteins in the toxin medium were separated using sodium dodecylsulphate polyacrylamide gel electrophoresis (SDS-PAGE). The gel was stained with Coomassie brilliant blue. The control medium was compared to Giardia sonicate (cytosolic contents), toxin medium that had *Giardia lamblia* growing in it for 3, 4, 5, 6, 7, 10, and 25 days as well as FCS. Media containing toxin contains proteins of approximate molecular weight of 22, 32, 38, 39, and greater than 97 kDa that were not present in the control media.

The Tris buffer and the membrane and cytoskeletal fractions from the sonicated trophozoites were negative for toxic activity. The cytosolic fraction resulted in cell death at the highest concentration and subsequent cell survival and elongation at lower concentrations. These findings were similar to the results obtained with GM.

The effect of bile on toxin production is shown in FIG. 12. Giardia grown in media containing bile produced a toxin, as measured by CHO cell elongation. Giardia grown in media without bile did not.

EXAMPLE 6

Adult Cat Immunization

An additional study was conducted to investigate the immunological response of adult cats to immunization with extracts of the 3 strains of *Giardia lamblia*. Twelve adult cats were immunized with sonicated *Giardia lamblia* strains WB (373 µg protein/mL) (n=4), S2 (864 µg protein/mL) (n=4), and D3 (120 µg protein/mL) (n=4). Cats were vaccinated subcutaneously, receiving 1.0 ml of vaccine which comprised 0.2 ml of the previously described adjuvant and 0.8 ml sonicate. The cats were boosted 21 days later and boosted a second time after an additional 21 days. A pre-immunization blood sample was taken and all cats were sampled for IgG ELISA 7 days after each booster immunization. The following table (Table 6) is a summary of the immunological data obtained from this study. Mature cats had a higher initial IgG titer to Giardia than the young kittens described in the above experiment (i.e. Table 2) and these adult cats responded to vaccination with a significant increase in IgG titer.

TABLE 6

Serum IgG Titers from Adult Cats Immunized With Giardia

| CAT NUMBER | STRAIN | PREIMMUNE TITER | DAY 28 TITER | DAY 42 TITER |
|---|---|---|---|---|
| 9 | WB | 128 | 1280 | nd |
| 10 | WB | 128 | 1600 | 1600 |
| 13 | WB | 128 | 128 | 800 |
| 14 | WB | 64 | 3200 | 3200 |
| 6 | S2 | 64 | 6400 | 3200 |
| 8 | S2 | 400 | 3200 | 3200 |
| 12 | S2 | 32 | 1280 | 6400 |
| 15 | S2 | 32 | 1280 | 1600 |
| 3 | D3 | 16 | 640 | 1600 |
| 5 | D3 | 64 | 640 | 1600 |
| 11 | D3 | 128 | 1280 | 800 |
| 18 | D3 | 128 | 640 | 3200 | nd = not done

Modification of the above-described modes of carrying out the various embodiments of this invention will be apparent to those skilled in the art following the teachings of this invention as set forth herein. The examples described above are not limiting, but are merely exemplary of this invention, the scope of which is defined by the following claims.

What is claimed is:

1. A method of preventing or treating a giardia infection in an animal comprising administering to said animal at least one dose of an effective amount of a giardia vaccine comprising giardia strain cultured in media containing bile so as to make it protectively immunogenic.

2. The method of claim 1 wherein said vaccine further comprises an adjuvant.

3. The method of claim 1 wherein said administration is parenteral or oral administration.

4. The method of claim 3 wherein said administration is parenteral and said parenteral administration comprises subcutaneous, intramuscular, intraperitoneal, or intravenous administration.

5. The method of claim 1 wherein said administration is performed two or more times.

6. The method of claim 5 wherein said administration comprises annual administration.

7. The method of claim 1 wherein said effective amount is sufficient to prevent colonization of the gut of said animal by said giardia.

8. The method of claim 1 wherein said effective amount is sufficient to prevent symptoms of giardiasis from occurring in said animal.

9. The method of claim 1 wherein said effective amount is sufficient to prevent shedding of giardia cysts in said animal.

10. The method of claim 1 wherein said effective amount is sufficient to prevent shedding of viable giardia cysts in said animal.

11. The method of claim 1 wherein said administration is to a symptomatic or asymptomatic animal and said effective amount is sufficient to increase growth rate of said animal.

12. The method of claim 1 wherein said animal is a human and said human exhibits chronic giardia infection.

13. The method of claim 1 wherein said administration is to an animal used for food production and said effective amount is sufficient to increase feed conversion in said animal.

* * * * *